United States Patent [19]

Walters

[11] Patent Number: 5,288,915
[45] Date of Patent: Feb. 22, 1994

[54] PROCESS OF MAKING KETONES

[75] Inventor: Marlin E. Walters, West Columbia, Tex.

[73] Assignee: The Dow Chemical Company, Midland, Tex.

[21] Appl. No.: 992,519

[22] Filed: Dec. 17, 1992

Related U.S. Application Data

[62] Division of Ser. No. 788,903, Nov. 7, 1991, abandoned.

[51] Int. Cl.$^5$ .............................................. C07C 45/43
[52] U.S. Cl. ..................... 568/323; 568/364; 568/394; 470/190; 470/196; 470/197
[58] Field of Search ............... 568/323, 364, 394, 310; 570/196, 190, 197, 198

[56] References Cited

U.S. PATENT DOCUMENTS

| | | | |
|---|---|---|---|
| 3,297,763 | 1/1967 | Slates et al. | 568/323 |
| 3,953,494 | 4/1976 | Meyers et al. | 568/319 |
| 3,992,432 | 11/1976 | Napier et al. | 568/319 |
| 4,297,514 | 10/1981 | Ma | 568/319 |
| 4,359,586 | 11/1982 | Ho et al. | 568/364 |
| 5,138,107 | 8/1992 | Sasson | 570/190 |

FOREIGN PATENT DOCUMENTS 0150169 7/1985 European Pat. Off. ............ 570/198

OTHER PUBLICATIONS

Ida Smedley in *J. Chem. Soc.* 87(1905) pp. 1249–1255.
Huntress, Hershberg and Cliff in *J. Am. Chem. Soc.*, pp. 2920–2724 (1931).
Ray and Albertson in *J. Am. Chem. Soc.*, 70, pp. 1154–1155 (1948).
Greenhow, Harris, and White in *J. Chem. Soc.*, pp. 3116–3121 (1954) (CA 50:263).
Ol'dekop and Kalinina in *Zhurnal Obshchei Khimii*, 30, pp. 3358–3361 (1960) (CA 55:18632).
Herbert O. House in *Modern Synthetic Reactions*, 3, pp. 156–162 (1965).
A. Brandstrom in "Principles of Phase-Transfer Catalysis by Quaternary Ammonium Salts" in V. Gold et al (ed) *Advances in Physical Organic Chemistry* (1977) pp. 267–330.
E. Dehmlow et al in *Tetrahedron Lett.* 27 (1977) pp. 2361–2364.
Meyers et al in *Cayalysis in Organic Syntheses* pp. 197–278 (1977).
Alneri, Bottaccio, and Carletti in *Tetrahedron Lett.* 24, pp. 2117–2118 (1977).
Janczyk, Kwast, and Makosza in *J. Org. Chem.*, 44 No. 7 (1979) pp. 1192–1194.
Lauritzen et al in *Acta Chemica Scandinavica* 35, pp. 263–268 (1981).
Dehmlow and Dehmlow in *Phase Transfer Catalysis* pp. 1–22 (1983).
Reeves et al in *Israel Journal of Chemistry* 26, pp. 225–228 (1985).
Chupp et al., in *Synthesis* 1986 (2) pp. 224–226.

*Primary Examiner*—James H. Reamer

[57] ABSTRACT

Ketones are prepared by admixing at least one gem-dichloro compound with at least one acid such that the ketone wherein the keto-oxygen replaces the gem-dichloro group is formed. The reaction is exemplified by the reaction of 9,9-dichlorofluorene with an acid such that fluorenone is formed. This process has the advantage that no oxidizing agent is used.

24 Claims, No Drawings

PROCESS OF MAKING KETONES

CROSS-REFERENCE TO RELATED APPLICATION

This is a divisional of application Ser. No. 07/788,903 filed Nov. 7, 1991 now abandoned.

This invention relates to ketones, and their preparation, in particular fluorenone and its preparation.

Fluorenone is useful as a starting material for making such compounds as dichlorofluorene, bis(hydroxyphenyl)fluorene and bis(aminophenyl)fluorene.

Fluorenone is typically prepared using oxidative methods. For instance, sodium dichromate is reported to oxidize fluorene in 60–70 percent yield (Huntress, et al. J Amer. Chem. Soc. 53, 275020, (1931) and Tanaka et al. Nippon Kagaku Kaishi, 1973, 126) Use of oxygen to oxidize fluorene is reported to give higher yield, but requires 24 hours. (Alneri, et al. Tetrahedron Letters, 24, 2117 (1977)). A multiphase system involving an organic phase, an aqueous sodium hydroxide phase and a catalyst of elemental carbon and phase transfer catalyst has also been reported in U.S. Pat. No. 4,297,514 (K. Ma). Oxidation of fluorene in air in pyridine in the presence of benzyltrimethylammonium hydroxide is reported to give a yield of 85 percent. (Sprinzak, J. Amer. Chem. Soc., 80, 5449, (1958). Oxygen was used to convert fluorene to fluorenone in dimethylsulfoxide, in the presence of sodium hydroxide over a five hour period to give a 99.8 percent yield. (U.S. Pat. No. 3,875,237 to Niznik.)

Each of these known methods for converting fluorene to fluorenone require oxidation including the use of oxidizing agents and require purification of the reaction product to obtain fluorenone.

It would be desirable to prepare fluorenone such that no oxidizing agent is required, advantageously such that high yields are obtained in short reaction times.

SUMMARY OF THE INVENTION

The invention is a process for preparing ketones comprising admixing at least one gem-dichloro compound with at least one acid such that a ketone is formed. The reaction is exemplified by the reaction of 9,9-dichlorofluorene with an acid such that fluorenone is formed.

This process has the advantage that no oxidizing agent is used. Advantageously, ketones such as fluorenone are also produced in high yield in a short time.

DETAILED DESCRIPTION OF THE INVENTION

The starting materials for the reaction are gem-dichloro compounds which can delocalize electron density, such as those having unsaturated substituents including vinyl, nitro, carbonyl, cyano, sulfone, or phenyl groups. These substituents have inductive electron withdrawing ability and the ability to delocalize negative charge. These gem-dichloro compounds are gem-dichloro derivatives of compounds often referred to as active methylene compounds. More preferred are compounds having a gem-dichloro group ($-CCl_2-$) adjacent at least one vinyl, nitro, carbonyl, cyano, sulfone, or phenyl group, most preferably adjacent at least two such groups. Exemplary of such compounds are 9,9-dichlorofluorene, 9,9-dichloro ring-substituted fluorenes, 1,1-dichloroindene, 9,9-dichloroxanthene, 10,10-dichloroanthrone, 1,1-dichlorocyclopentadiene, 1,1-dichloroacetone, α,α-dichloroacetophenone, α,α-dichlorodeoxybenzoin, α,α-dichlorophenylacetonitrile, 9,9,10,10-tetrachlorodihydroanthracene, 1,1-dichloro-1-phenyl-2-propanone and the like. Such gem-dichloro target compounds are unsubstituted or inertly substituted, that is having substituents which do not undesirably interfere with the chlorination or subsequent reactions. Such substituents include alkyl, halo, nitro, cyano, carboxyl, thio, sulfoxide, sulfone, carbonyl, ether, and aryl groups, as well as other substituents not having a hydroxyl, primary or secondary amino, or mercapto group. Preferred gem-dichloro compounds include 9,9-dichlorofluorene, 1,1-dichloro indene, 9,9,-dichloroxanthene with 9,9-dichlorofluorene being most preferred. Such compounds are commercially available or are suitably made by any means within the skill in the art, such as by the process of Ida Smedley, who reported a preparation of 9,9-dichlorofluorene in 1905 from heating fluorenone and a slight excess of phosphorus pentachloride (J. Chem. Soc. 87, 1249 (1905); by Ray et al. who report following Smedley's method and attaining a 66 percent yield. (J Amer. Chem. Soc., 70, 1954 (1948).); or by Reeves et al. in Israel J. Chem. 26. 225, (1985) where tetrabutylammonium bromide was used as a phase transfer catalyst to chlorinate fluorene using carbon tetrachloride in an organic phase as chlorine source with an aqueous hydroxide phase to convert fluorene in a 51.9 percent yield to 9,9-dichlorofluorene. Preferably, the method used to obtain the gem-dichloro compound is that disclosed in copending application Ser. No. 07/789,232 filed Nov. 7, 1991, abandoned for continuation Ser. No. 08/9,057 filed Jul. 12, 1993 which is incorporated by reference herein in its entirety. In that process, a compound which has acidic protons and a molecular structure which can delocalize the electron density of a conjugate base is chlorinated using a perchloroalkane such as carbon tetrachloride and aqueous base in the presence of a tetraalkylammonium or tetraalkylphosphonium hydroxide phase transfer catalyst.

The gem-dichloro compound is admixed with an acid such that a ketone is formed. Any conditions under which the reaction takes place are suitably used.

Any acid which results in the formation of a ketone is suitably used. The acid is preferably a mineral acid, but suitably is optionally an organic acid, preferably one having a pKa of at most about 14.0, more preferably at most about 5. The acid is preferably, but optionally, in aqueous solution but is suitably alternatively either a liquid which is miscible in the reaction medium or a solid acidic material such as silica gel, alumina or an acid clay or an organic resin with bound acid functionality such as sulfonic acid cation exchange resin commercially available from The Dow Chemical Company under the trade designation MSC-1 or a salt with Lewis Acid properties such as $AlCl_3$ or $FeCl_3$. In aqueous solution, the acid is suitably present in any effective concentration, but preferably in a concentration at least sufficient to promote the reaction at a desirable rate and insufficient to cause excessive or uncontrollable exothermic heating of the reaction mixture, in a concentration of from about 0.001 to about 1000, more preferably from about 0.01 to about 100, most preferably from about 0.1 to about 10 based on the moles of dichloro compound. An organic acid is optionally used in a concentration such that there is at least one molar equivalent of water for each mole of gem-dichloro compound but preferably in the designated concentrations.

In the practice of the invention, at least about one mole of water for each mole of gem-dichloro compound to be converted to a ketone is needed but preferably water is present in an amount such that the reaction proceeds at a rate which is sufficient to complete the reaction in a predetermined time, but insufficient to require excessive amounts of acid to maintain a pH below about 5.0.

The length of time required for the reaction depends on the acidity of the acid. Extended exposure (about 20 hours) to aluminum oxide, activated, neutral (pH of aqueous suspension 7.0±0.5) is sufficient to hydrolyze a solution of dichlorofluorene to 9-fluorenone. More acidic acids increase the rate of hydrolysis. Acids such as sulfuric require only 15 minutes to convert 9,9-dichlorofluorene to the ketone.

While any effective amount of acid is suitably used, preferably the acid is used in an amount sufficient to promote the desired reaction in the desired time but insufficient to cause uncontrollable exothermic heating, more preferably in an amount of from about 0.01 to about 100, most preferably from about 0.1 to about 10 equivalents based on equivalents of gem-dichloro compound wherein one equivalent is one/half mole since each mole has two chlorine atoms.

Especially when the acid is used in an aqueous solution, there is optionally, and preferably, a solvent for the gem-dichloro compound. Suitable solvents include those which are stable to acid; exemplary solvents include aromatic solvents such as benzene, ethylbenzene, cumene, toluene, xylene; chlorinated aromatics, chloroalkanes, ethers such as tetrahydrofuran; nitriles such as acetonitrile or benzonitrile; DMSO (dimethylsulfoxide), carbon tetrachloride; and the lower aliphatic carboxylic acids such as acetic acid, haloacetic, propionic and butyric acids, which optionally serve as both solvent and catalyst; preferably ethylbenzene, tolulene, cumene xylene, methylene chloride, tetrachloroethylene, dichloroethane, tetrahydrofuran, acetonitrile, DMSO, the listed carboxylic acids, carbon tetrachloride or mixtures thereof. When a gem-dichloro compound is prepared in carbon tetrachloride or another solvent, that solvent is preferably used in the process of the invention. While the gem-dichloro compound is optionally isolated from the solvent, or otherwise purified, such purification or isolation is unnecessary, especially when the gem-dichloro compound is prepared by the process disclosed in copending U.S. application Ser. No. 789,232 (filed Nov. 7, 1991 abandoned for continuation Ser. No. 08/9,057).

When an additional solvent is used, it is preferably one which is miscible with the perchloroalkane and which dissolves the target compound and, conveniently, is not undesirably affected by the reaction conditions. Such solvents include methylene chloride, ethylbenzene, cumene, chlorobenzene, tetrahydrofuran and the like. Such a solvent is conveniently used in an amount sufficient to obtain the maximum concentration of the target compound but not so little that the product would precipitate from the reaction mixture.

In the formation of ketones from gem-dichloro compounds according to the practice of the invention, use of a phase transfer catalyst is optional. When the gem-dichloro compound is obtained by a chlorination process involving phase transfer catalysts, the phase transfer catalyst is conveniently left with the gem-dichloro compound.

When an acid is added to a quaternary hydroxide, the quaternary ammonium salt of the acid's conjugate base is formed. This salt may act as a phase transfer catalyst for the hydrolysis (ketone formation) by providing a higher concentration of the acid in the organic phase, especially by extraction of the acid into the organic phase by "extraction by hydrogen bonding" where ion pairs are involved [Q+X−... HX]. See E. V. Dehmlow and S. S. Dehmlow, Phase Transfer Catalysis, Weinheim, Deerfield Beach, (Fla.) Basel: Verlag Chemie, 1980, pp. 15. For instance, when the acid is sulfuric acid and the phase transfer catalyst is represented by Q+OH−, the formation of the salt of the acid's conjugate base can be represented as:

$$Q^+OH^- + H_2SO_4 \rightleftharpoons Q^+HSO_4^- + H_2O$$

When the aqueous acid is not sufficiently soluble in the solvent containing dichlorofluorene, a phase transfer catalyst is preferably used. Any phase transfer catalyst within the skill in the art which accelerates the desired reaction is suitably used. Good yields and low reaction times are noted when the phase transfer catalyst is a tetraalkylammonium or tetraalkylphosphonium hydroxide, halide (e.g. bromide or chloride) or bisulfate such as tetrabutylammonium hydroxide, tetramethylammonium hydroxide, tetraethylammonium hydroxide, tetrapropylammonium hydroxide, benzyltrimethylammonium hydroxide, tributylmethylammonium hydroxide, the corresponding halides or bisulfate and the like, or the corresponding tetraalkylphosphonium salts. Preferably the phase transfer catalyst is a tetraalkylammonium hydroxide wherein all alkyl groups have from about 1 to about 20 carbon atoms and are non-aromatic, more preferably the tetraalkylammonium salt is tetrabutylammonium salt or tributylmethylammonium salt, most preferably tetra-n-butylammonium salt because this catalyst brings the reaction to completion in the shortest time with the least amount of catalyst relative to the target compound. Phase transfer catalysts in forms other than the hydroxide, e.g. the bromide or chloride are suitably used for formation of the ketone, especially since the acid used in ketone formation neutralizes at least a portion of the hydroxide. Such salts as the halide salts are readily available and, thus, are very useful when there is insufficient phase transfer catalyst in the gem-dichloro compound. The hydroxide is very advantageous in forming the gem-dichloro compound, and is, thus, preferred for use herein, to avoid separation thereof from the em-dichloro compound.

The phase transfer catalyst, when present, is suitably present in any amount sufficient to give a desired or predetermined rate of reaction, advantageously at least about 0.0001 mole ratio, preferably from about 0.0001 to about 1, more preferably from about 0.001 to about 0.1, most preferably from about 0.001 to about 0.05 molar ratio based on the number of moles of the target compound because this amount gives an acceptable rate of reaction and using more generally costs more and makes purification of the product more difficult.

Conveniently, the gem-dichloro compound is dissolved in a solvent therefor if one is to be used or is used neat is admixed with the phase transfer agent if used and the acid (optionally and preferably in aqueous solution) and if additional water is needed, water, in any order, simultaneously but separately or in admixture to form a reaction mixture. This order is convenient because a solution of dichlorofluorene prepared by the preferred method already contains the phase transfer agent. Alternatively, the reagents are suitably mixed in any order such that all reactants are present at one time.

The reaction mixture is preferably agitated by any means effective to contact the phases such that reaction occurs.

For relatively shorter reaction times, relatively faster mixing is preferred. While mixing is difficult to quantify, in a situation with relatively constant viscosities, power per unit volume (here watts/liter) is indicative of the amount of mixing. Thus, in the practice of the invention, mixing preferably involves use of at least about 0.8 W/l, more preferably at least about 15 W/l, most preferably at least about 100 W/l. Such mixing is suitably accomplished by any means within the skill in the art such as by rotary, static (e.g. recirculating, e.g. by pump) or other mixing.

The reaction is preferably carried out using non-metallic vessels and equipment, that is not having exposed metals, because metals such as iron (including steel, even stainless steels such as those designated as 304 on 316 stainless steel), nickel and titanium are observed to inhibit the reaction. The term non-metallic vessels and equipment is used to include vessels and equipment lined with non-metallic materials such as polymers (including plastics, resins and glass). Thus the reaction preferably occurs in the substantial absence of such metals, that is in the absence of sufficient metal to undesirably inhibit the reaction, more preferably in the absence of other than incidentally present (not deliberately added) metals particularly iron, including 304 stainless steel and 316 stainless steel. These metals are believed to inhibit the tetraalkylammonium hydroxides; thus use of additional tetraalkylammonium hydroxide to replace that which is inhibited permits reaction in the presence of metals.

The product can be isolated by means within the skill in the art, preferably by washing the solution with water to remove catalyst, then evaporating the solvent. Products are usually solids and are optionally purified by crystallization.

The reaction is allowed to go to a predetermined degree of completeness, advantageously to completion as determined by cessation of an increase in concentration of product. At temperatures such as about 30° C., completion is observed after about 1 minute to 3 hours depending on catalyst concentration, caustic concentration, and degree of agitation or mixing.

Any reaction conditions under which the reaction takes place are suitable, but preferred temperatures are from about 0° C. to about 200° C., more preferably from about 25° C. to about 175° C. most preferably from about 40° C. to about 100° C. because the reaction proceeds rapidly and there is little degradation of the catalyst. Any effective pressure is suitable, for instance from about 0.01 atmospheres (1 kPa) to hundreds of atmospheres; but at or near atmospheric pressure (100 kPa) is generally convenient. When gaseous acids such as HCl (hydrochloric acid) are used, the pressure is advantageously 1-200 atmospheres (100-20,000 kPa).

When a high purity product is desired it is often preferable to exclude oxygen, and preferably other oxidizing agents such as chromate from the reaction. Oxidizing agents often lead to over oxidized products, such as carboxcylic acids. Oxygen is suitably excluded by any means within the skill in the art such as by maintaining a nitrogen blanket over the reaction mixture, such as by nitrogen sparging. Other inert gases or vapors of volatile organic compounds or of hydrogen halides are suitably used to displace oxygen-containing gases.

The reaction is allowed to go to a predetermined degree of completeness, advantageously to completion as determined by cessation of an increase in concentration of product. At temperatures such as about 30° C., completion i-s observed after about 15 to 20 minutes. In general, short reaction times relative to those required to attain similar yields in oxidation reactions are observed to be attainable in the practice of the invention. Under conditions of 30° C., 9,9-dichlorofluorene in a 15 weight percent solution in carbon tetrachloride (CCl$_4$) with H$_2$SO$_4$ (9 M in water) in a molar ratio of 0.5, tetrabutylammonium hydrogen sulfate (0.047 M), the reaction times needed to achieve about 97 percent completion based on moles of starting dichlorofluorene are advantageously less than about 180 minutes, preferably less than about 60 minutes, more preferably less than about 30 minutes, most preferably less than about 15 minutes.

Relative to the corresponding oxidation reactions to produce fluorenone from fluorene, the practice of the invention is observed to result in high yields. For instance, under conditions of 30° C., 9,9-dichlorofluorene in a 15 weight percent solution in carbon tetrachloride (CCl$_4$) with H$_2$SO$_4$ (9 M in water) in a molar ratio of 0.5, tetrabutylammonium hydrogen sulfate (0.047 M), the reaction times needed to achieve about 97 percent completion based on moles of starting dichlorofluorene are advantageously less than about 180 minutes, preferably less than about 60 minutes, more preferably less than about 30 minutes, most preferably less than about 15 minutes, the yields obtained in reaction times of about 30 minutes are advantageously greater than about 50 percent, preferably greater than about 60 percent more preferably greater than about 75 percent, most preferably greater about 95 percent.

The combination of high yield and fast reaction rate facilitate the practice of the invention in either batch or continuous mode. For instance, reactants may be mixed and allowed to react very quickly while flowing through a reactor. The product is suitably, optionally, isolated or purified by means within the skill in the art after reaction.

The high yield indicates that there are relatively fewer byproducts and/or less starting materials in the product to be removed after reaction; therefore, purification or isolation of the product is simplified. Ease of isolation is ascribed to fewer oxidation by products as are produced in other methods. For instance, there is no chromate salt to remove, nor any solid residues like charcoal. Methods of isolation are within the skill in the art and include crystallization, distillation, solvent extraction, filtration and the like.

The following examples are given to illustrate, but not limit the invention. In the examples, all parts, ratios and percentages are by weight unless specified otherwise. Examples of the invention (EX.) are designated numerically.

EXAMPLE 1

Preparation of 9-Fluorenone from Fluorene.

The reactor is a 1000 mL cylinder 4 inches (100 mm) in diameter by 5.5 inches (1–40 mm) in height equipped with a 2 inch (50 mm) diameter turbine impeller driven by a vertical shaft. Stirring rate is measured by a tachometer. Temperature is controlled by an internal heat exchanger which is a 10 foot (3.048 m) by 0.25 inch (0.635 cm) external diameter coil immersed in the reaction medium through which coolant is pumped, maintained at a constant temperature by a circulating refrigerated/heated bath outside of the apparatus.

The temperature is measured by a thermocouple inside a thermowell which runs the entire depth of the reactor. The reactor is also equipped with a nitrogen inlet which is used to maintain a nitrogen atmosphere above the reaction solution. The entire apparatus is made from fluorocarbon polymer commercially available from E. I. du Pont de Nemours & Co. under the trade designation Teflon PFA.

The reactor is flushed with nitrogen. A solution of fluorene (49.87 g, 0.300 mole) and carbon tetrachloride (CCl$_4$) (448.79 g, 2.9177 mole, 281.55 mL) is charged to the reactor followed by sodium hydroxide (NaOH) (30 weight percent solution in water, 80.00 g, 0.60 mole, 60.15 mL, 24.00 g dry wt.). The stirrer is started and the speed adjusted to 2500 revolutions per minute (rpm). The coolant is admitted to the coils, and the temperature of the reaction solution is adjusted to 30° C. The catalyst, tetrabutylammonium hydroxide (40 weight percent solution in water, 3.89 g, 0.006 mole, 3.85 mL) is added at once. The reaction mixture is sampled after 15 minutes and analyzed by gas chromatography (GC) on a gas chromatograph commercially available from Varian Associates under the trade designation Varian 3400 GC, equipped with a 30 meter by 0.53 mm capillary column commercially available from J&W Scientific under the trade designation Megabore coated with a 1 micron (0.0001 cm) film of poly trifluoropropyl co dimethylsiloxane commercially available from J&W Scientific under the trade designation DB-210 as the stationary phase and a flame ionization detector (FID) (commercially available from Varian Associates under the trade designation Varian 3400), which shows that the reaction mixture after 15 minutes contains 0.27 percent fluorene, 97.26 percent 9,9-dichlorofluorene, and 2.46 percent 9-fluorenone (all percentages by weight).

The stirring is stopped, the phases are allowed to separate, and the aqueous phase is removed from the reactor. The stirrer is started and its speed adjusted to 500 rpm. Sulfuric acid (46.025 g, 0.469 mole, 25.0 mL) is added to the reactor and stirring continued. After 4 hours, the reaction mixture is sampled and analyzed by GC which shows the composition of the mixture to be 92.21 percent 9-fluorenone, and 7.78 percent 9,9-dichlorofluorene (all percentages by weight). The reaction mixture is allowed to stir overnight and, again, sampled and analyzed by GC, which detected no 9,9-dichlorofluorene; the only product present is 9-fluorenone, (100 percent).

EXAMPLE 2

The reactor described in Example 1 is flushed with nitrogen. A solution of fluorene (33.24 g, 0.200 mole) and carbon tetrachloride (299.20 g, 1.9451 mole, 187.70 mL) is charged into the reactor followed by NAOH (30 weight percent solution in water, 53.33 g, 0.40 mole, 40.10 mL, 16.00 g dry weight). The stirrer is started, and the speed, adjusted to 4000 rpm. The coolant is admitted to the coils, and the temperature of the reaction solution is adjusted to 30° C. The catalyst, tetrabutylammonium hydroxide (40 weight percent solution in water, 2.59 g, 0.004 mole, 2.57 mL) is added at once. The reaction mixture is sampled after 15 minutes and analyzed by GC which shows that the reaction mixture contains 0.27 percent fluorene, 97.26 percent 9,9-dichlorofluorene, and 2.46 percent 9-fluorenone (all percentages by weight). Sulfuric acid (80.07 g 98 percent by weight concentration, 0.8000 mole, 42.62 mL) is added to the reactor and stirring continued. After 15 minutes, the reaction mixture is sampled and analyzed by GC which shows the composition of the mixture to now be 97.850 percent 9-fluorenone, and 2.150 percent 9,9-dichlorofluorene by weight. The reaction mixture is allowed to stir overnight and, again, sampled and analyzed by GC which shows no 9,9-dichlorofluorene; the only product is present is 9-fluorenone, 100 percent.

This example shows that separation of phases is not necessary prior to the addition of the acid.

What is claimed is:

1. A process for preparing a ketone comprising reacting a compound having acidic protons and a molecular structure which can delocalize the electron density of a conjugate base with a perchloroalkane and aqueous base in the presence of a tetraalkylammonium or tetraalkylphosphonium hydroxide phase transfer catalyst to form at least one gem-dichloro compound; and (b) admixing the gem-dichloro compound with an effective amount of at least one acid in the presence of at least about one mole of water for each mole of gem-dichloro compound such that a ketone is formed.

2. The process of claim 1 wherein the acid is an inorganic acid.

3. The process of claim 1 wherein the acid is an organic acid.

4. The process of claim 1 wherein the acid is selected from sulfuric, hydrochloric, hydrobromic, acetic, chloroacetic, trichloroacetic, methanesulfonic, propionic acid and mixtures thereof.

5. The process of claim 1 wherein the acid has a pKa of less than about 14.

6. The process of claim 5 wherein the acid has a pKa of less than about 5.

7. The process of claim 1 wherein the acid is a solid acidic material.

8. The process of claim 1 wherein the acid is silica gel, alumina or an acid clay, or an organic resin with bound acid functionality.

9. The process of claim 8 wherein the bound acid functionality comprises sulfonic acid groups.

10. The process of claim 8 wherein the bound acid functionality is sulfonic acid groups, carboxylic acid groups or mixtures thereof.

11. The process of claim 1 wherein the acid is a salt with Lewis Acid properties.

12. The process of claim 1 wherein the acid is present in an amount of from about 0.01 to about 100 equivalents per equivalent of gem-dichloro compound.

13. The process of claim 1 wherein the gem-dichloro compound has chlorine atoms replacing the hydrogen atoms of an active methylene group.

14. The process of claim 1 wherein the gem-dichloro compound has chlorine atoms on a carbon also substituted with at least one group selected from vinyl, nitro, carbonyl, cyano, sulfone, or phenyl groups.

15. The process of claim 1 wherein the gem-dichloro compound is an unsubstituted or inertly substituted 9,9-dichlorofluorene, 1,1-dichloroindene, 9,9-dichloroxanthene, 10,10-dichloroanthrone, 1,1-dichlorocyclopentadiene, 1,1-dichloroacetone, α,α-dichloroacetophenone, α,α-dichlorodeoxybenzoin, α,α-dichlorophenylacetonitrile, 9,9,10,10-tetrachlorodiydroanthracene, 1,1-dichloro-1-phenyl-2-propanone or mixture thereof.

16. The process of claim 15 wherein the gem-dichloro compound is 9,9-dichlorofluorene, and the ketone is fluorenone.

17. The process of claim 2 wherein the gem-dichloro compound is 9,9-dichlorofluorene, and the ketone is fluorenone.

18. The process of claim 1 wherein there is present a phase transfer compound.

19. The process of claim 18 wherein the phase transfer compound is a tetraalkyl- ammonium or -phosphonium salt.

20. The process of claim 19 wherein the phase transfer compound is a tetraalkyl- ammonium or -phosphonium hydroxide, halide, or bisulfate.

21. The process of claim 20 wherein the phase transfer compound is a tetraalkylammonium hydroxide, or halide, or bisulfate.

22. A process for preparing a ketone comprising admixing the reaction product of a compound which has acidic protons and a molecular structure which can delocalize the electron density of a conjugate base, perchloroalkane, and aqueous base in the presence of a phase transfer catalyst which is a tetraalkyl-ammonium or -phosphonium salt with an acid such that a ketone is is formed.

23. The process of claim 22 wherein the compound which has acidic protons and a molecular structure which can delocalize the electron density of a conjugate base is fluorene, the perchloroalkane is carbon tetrachloride, the phase transfer catalyst is a tetraalkylammonium or -phosphonium hydroxide and the ketone is 9-fluorenone.

24. A process for preparing a ketone comprising (a) reacting a compound having acidic protons and a molecular structure which can delocalize the electron density of a conjugate base, said compound having the acidic protons on a saturated carbon atom which also has at least one substituent selected from vinyl, nitro, carbonyl, cyano, sulfone or phenyl groups, with a perchloroalkane and aqueous base in the presence of a tetraalkylammonium or tetraalkylphosphonium hydroxide phase transfer catalyst to form at least one gem-dichloro compound; and (b) admixing the gem-dichloro compound having a gem-dichloro group adjacent at least one vinyl, nitro, carbonyl, cyano, sulfone, or phenyl group with an effective amount of at least one acid or pKa at most about 14 in the presence of at least about one mole of water for each mole of gem-dichloro compound such that a ketone is formed.

* * * * *